US00PP11144P

United States Patent [19]

Walden

[11] Patent Number: Plant 11,144

[45] Date of Patent: Dec. 7, 1999

[54] MINIATURE ROSE PLANT NAMED 'JACSOME'

[75] Inventor: John K. Walden, Thousand Oaks, Calif.

[73] Assignee: Bear Creek Gardens, Inc., Medford, Oreg.

[21] Appl. No.: 09/052,800

[22] Filed: Mar. 31, 1998

[51] Int. Cl.[6] ..... A01H 5/00

[52] U.S. Cl. ..... Plt./123

[58] Field of Search ..... Plt./123, 129, 116, Plt./122

[56] References Cited

U.S. PATENT DOCUMENTS

P.P. 5,770 7/1986 De Ruiter ..... Plt./122

*Primary Examiner*—Howard J. Locker

*Attorney, Agent, or Firm*—Klarquist Sparkman Campbell Leigh & Whinston LLP

[57] ABSTRACT

A miniature rose plant having mauve pink color; long, pointed ovoid bud form; medium-hard petal substance; forcing well as a pot rose; and having outstanding blossom life.

1 Drawing Sheet

The present invention relates to a new and distinct variety of rose plant of the miniature class which was originated by me by crossing an unnamed seedling (whose parents are unnamed seedling×RUImired U.S. Plant Pat. No. 5,770), with the variety 'SAVawin', U.S. Plant Pat. No. 5,691.

The primary objective of this breeding was to produce a new miniature rose variety having mauve color; hybrid tea bud form, hard petal substance, long post-harvest life, clustering of flowers, and can be grown and forced in a greenhouse as a pot rose. The objective was substantially achieved, along with other desirable improvements, as evidenced by the following unique combination of characteristics that are outstanding in the new variety and that distinguish it from its parents, as well as from all other varieties of which I am aware:

1. Mauve pink color;
2. Long, pointed ovoid bud form;
3. Medium hard petal substance;
4. Production of small clusters of flowers;
5. Forces well as a pot rose; and
6. Outstanding life of blossoms as pot rose.

Asexual reproduction of this new variety by cuttings, as performed at Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling (unnamed seedling× RUImired, U.S. Plant Pat. No. 5,770).

*Pollen parent.*—'SAVawin' (U.S. Plant Pat. No. 5,691).

Classification:

*Botanical.*—Rosa hybrida.

*Commercial.*—Miniature rose.

FLOWER

Observations made in January 1998, from specimens grown in a greenhouse environment at Somis, Calif.

Blooming habit: Recurrent.

Bud:

*Size.*—About ¾ inch long when the petals start to unfurl.

*Form.*—The bud form is long, pointed ovoid.

*Color.*—When sepals first divide, bud color is Red-Purple Group 61B. When half blown, the upper sides of the petals are Red-Purple Group 66A, and the lower sides of the petals are Red-Purple Group 61C.

*Sepals.*—Color: Yellow-Green Group 144A. Surface texture: Smooth to slightly rough. There are three very lightly appendaged sepals. There are two unappendaged sepals with hairy edges.

*Receptacle.*—Color: Yellow-Green Group 144A. Shape: Pear. Size: Small (about 5/16"×3/16"). Surface: Smooth.

*Peduncle.*—Length: Short (⅞–1"). Surface: Smooth to slightly rough, occasionally small glandular appendages are present on basal shoots. Color: Yellow-Green Group 144A. Strength: Erect; slender.

Bloom:

*Size.*—Small. Average open size is 2 to 2¼ inches.

*Borne.*—Singly and several together in clusters of 3–5 blooms, Pyramidal to irregular shape.

*Stems.*—Short to normal. Average length is about 11 inches.

*Form.*—When first open: High centered. Permanence: Flattens; outer petal edges quill moderately.

*Petalage.*—Number of petals under normal conditions: 25–30.

*Color.*—The upper sides of the petals are Red-Purple Group 61C, lightening towards center to Red-Purple Group 57D. The reverse sides of the petals are Red-Purple Group 57C. The base of each petal has a small (3/16"×3/16"), deltoid, White Group 155A spot at point of attachment. The major color on the upper sides is Red-Purple Group 61C.

*Variegations.*—None.

*Discoloration.*—At the end of the first day: Unchanged. At the end of the third day: Unchanged.

*Fragrance.*—Slight.

Petals:

*Texture.*—Leathery.

*Shape.*—Deltoid.

*Form.*—Edges slightly quilled.

*Arrangement.*—Imbricated; shingle like. Petaloids in the center are few (2 to 4 ).

*Persistence.*—Petals drop off cleanly before drying.

*Lastingness.*—On the plant: Long (16–18 days). As a cut flower: Not tested.

Reproductive Parts:

*Anthers.*—Size: Medium. Quantity: Many. Color: Pinkish white, yellow on edges. Arrangement: Regular around styles.

*Filaments.*—Color: Yellow.

*Pollen.*—Color: Gold-yellow.

*Styles.*—Color: Reddish pink (near Red Group 47C).

*Stigmas.*—Color: White.

Plant:

*Form.*—Bush.

*Growth.*—Medium; upright.

*Mature Plant.*—Height: 24 inches. Width: 20 inches.

Foliage: Number of leaflets on normal mid-stem leaves: Seven.

*Size.13* Medium (4¼ inches long×2⅜ inches wide).

*Quantity.*—Normal.

*Color.*—New foliage: Upper and lower surface: Close to Greyed-Purple Group 185A, quickly changing to green. Old foliage: Upper surface: Green Group 137A. Lower surface: Near Yellow-Green Group 148B.

*Shape.*—Broadly oval.

*Texture.*—Upper side: Leathery. Semi-glossy when young, maturing to a matte finish or sheen.

*Edge.*—Serrated.

*Serration.*—Single.

*Petiole rachis.*—Color: Reddish when young, changing quickly to Yellow-Green Group 146C.

*Petiole Underside.*—With prickles.

*Stipules.*—Short (about ½" long), serrated.

*Disease resistance.*—Resistant to mildew under normal growing conditions at Somis, Calif. and Wasco, Calif.

Wood:

*New wood.*—Color: Yellow-Green Group 144B. Bark: Smooth.

*Old wood.*—Color: Near Yellow-Green Group 146B. Bark: Smooth.

Prickles:

*Quantity.*—On main canes from base: Ordinary. On laterals from main canes: Ordinary.

*Form.*—Short (¼"); slightly hooked downward.

*Color when young.*—Greyed-Orange Group 171C.

Small prickles:

*Quantity.*—On main stalks: None. On laterals: None.

I claim:

1. A novel rose plant of the miniature class as herein shown and described, characterized particularly as to novelty by its mauve pink color; long, pointed ovoid bud form; medium-hard petal substance; forcing well as a pot rose; and having outstanding blossom life.

* * * * *

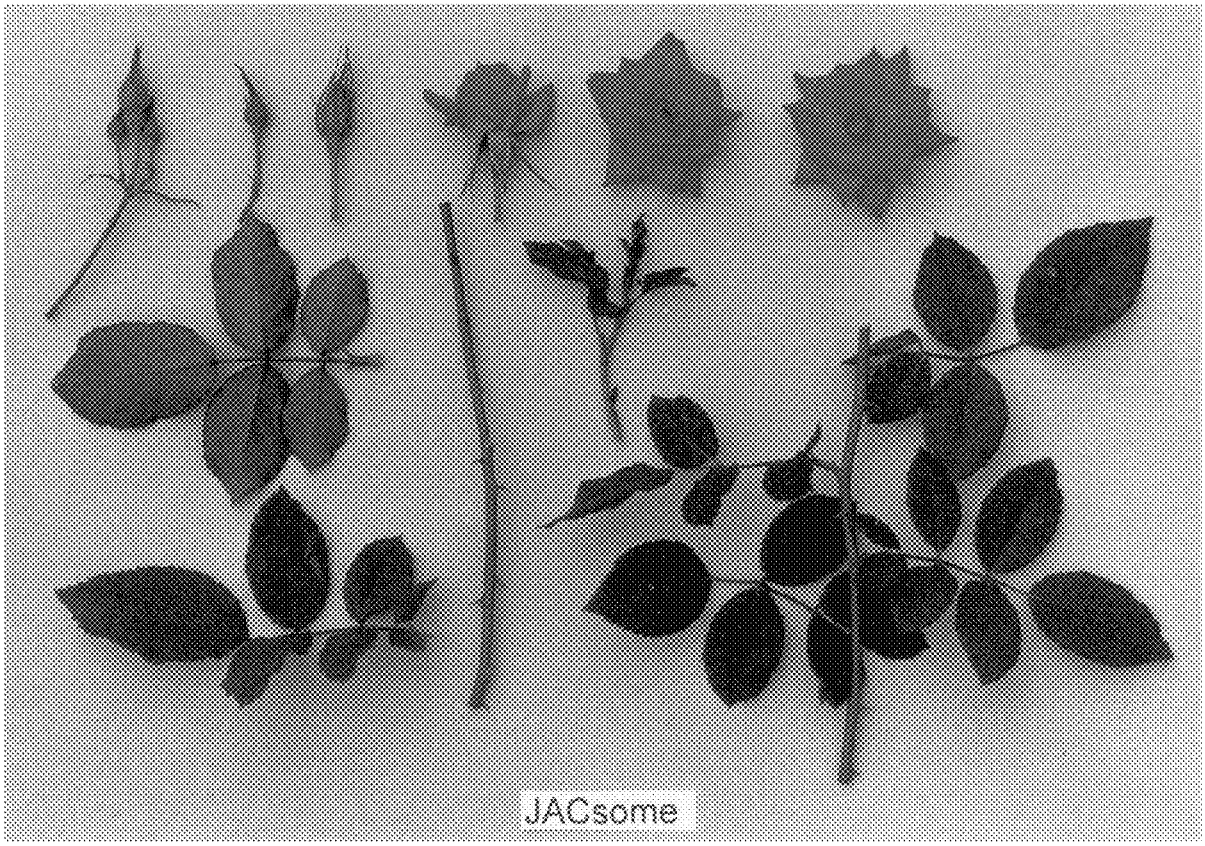
JACsome

UNITED STATES PATENT AND TRADEMARK OFFICE

CERTIFICATE OF CORRECTION

PATENT NO. : PP11,144
DATED : December 7, 1999
INVENTOR(S) : John K. Walden

It is certified that error appears in the above-identified patent and that said Letters Patent is hereby corrected as shown below:

In the Specification:

Column 3,
Line 20, reads "Size.13 Medium". It should read -- Size.-Medium --.

Signed and Sealed this

Tenth Day of July, 2001

*Attest:*

Nicholas P. Godici

*Attesting Officer*

NICHOLAS P. GODICI
*Acting Director of the United States Patent and Trademark Office*